(12) United States Patent
Tracey et al.

(10) Patent No.: US 6,423,705 B1
(45) Date of Patent: Jul. 23, 2002

(54) COMBINATION THERAPY

(75) Inventors: Wayne R. Tracey, Niantic; Roger J. Hill, Salem, both of CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/052,320

(22) Filed: Jan. 17, 2002

Related U.S. Application Data

(60) Provisional application No. 60/264,173, filed on Jan. 25, 2001.

(51) Int. Cl.[7] .................... A61K 31/55; A61K 31/495; A61K 31/445; A61K 31/155

(52) U.S. Cl. ................. 514/221; 514/252.13; 514/331; 514/634

(58) Field of Search ................. 514/221, 252.13, 514/331, 634

(56) References Cited

FOREIGN PATENT DOCUMENTS

| CA | 2227112 | 1/1998 | ......... C07D/231/10 |
|----|---------|--------|------------------------|
| CA | 2245776 | 8/1998 | ......... A61K/31/445 |
| WO | WO9746226 | 11/1997 | ......... A61K/31/155 |
| WO | WO9943663 | 2/1999 | ......... C07D/249/06 |

*Primary Examiner*—Raymond Henley, III
(74) *Attorney, Agent, or Firm*—Peter C. Richardson; Gregg C. Benson; Carl J. Goddard

(57) ABSTRACT

The invention provdes methods of reducing tissue damage resulting from ischemia which comprise administering to a mammal in need of such reduction an effective amount of a combination, or a pharmaceutical composition comprising Such combination, of an NHE-1 inhibitor and a second compound selected from the group consisting of: (a) a complement modulator, (b) a metabolic modulator, (c) an anti-apoptotic agent, (d) a nitric oxide synthase-related agent, and (e) an enzyme/protein modulator. The invention further provides pharmaceutical compositions comprising an amount of an NHE-1 inhibitor; an amount of a second compound selected from the group consisting of (a) a complement modulator, (b) a metabolic modulator, (c) an anti-apoptotic agent, (d) a nitric oxide synthase-related agent, and an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor; and, preferably, a pharmaceutically acceptable pharmaceutically acceptable carrier, vehicle, or diluent.

31 Claims, No Drawings

COMBINATION THERAPY

CROSS REFERENCE TO RELATED APPLICATION

This application claims the benefit of U.S. Provisional Application No. 60/264,173, Jan. 25, 2001.

FIELD OF THE INVENTION

The invention relates to methods of reducing tissue damage resulting from ischemia using a combination, or a pharmaceutical composition of such combination, of a sodium/hydrogen exchange type-1 (NHE-1) inhibitor and a second compound selected from the group consisting of: (a) a complement modulator, (b) a metabolic modulator, (c) an anti-apoptotic agent, (d) a nitric oxide synthase-related agent, and (e) an enzyme/protein modulator. The invention further provides kits directed to such combinations.

BACKGROUND OF THE INVENTION

Ischemic injury, particularly to that of the myocardium, can occur in out patients as well as in perioperative settings and can lead to the development of sudden death, myocardial infarction, or congestive heart failure. There is currently an unmet medical need to prevent or minimize myocardial ischemic injury, particularly perioperative myocardial infarction. Such therapy is anticipated to be life-saving and reduce the need for hospitalization, enhance quality of life and reduce overall health care costs of high risk patients.

Pharmacological cardioprotection would reduce the incidence and progression of myocardial infarction and dysfunction occurring in these perioperative surgical settings. In addition to reducing myocardial damage and improving postischemic myocardial function in patients with ischemic heart disease, cardioprotection would also decrease the incidence of cardiac morbidity and mortality due to myocardial infarction and dysfunction in "at risk" patients (i.e., those patients greater than 65 years of age, exercise intolerant, those suffering from coronary artery disease, diabetes mellitus, or hypertension, and the like) that require non-cardiac surgery.

In response thereto, numerous therapeutic regimens have been developed, for example, the use of compounds that inhibit the sodium/hydrogen exchange type-1 (NHE-1) transport system. The mechanism by which NHE-1 inhibitors elicit protective effects against ischemia, particularly that affecting the myocardium, consists of a reduction in the increased sodium ion influx which is caused in reperfused/hypoperfused tissues due to intracellular acidification and subsequent activation of the sodium/hydrogen exchange transport system. This results in a delay of sodium overload of the tissue. Since sodium and calcium ion transport are coupled in cardiac tissue, this also prevents the life-threatening calcium overload of myocardial cells.

The use of NHE-1 inhibitors in combination with certain other therapeutic agents is generally known. For example, EPO 0 918 515 discloses the use of NHE-1 inhibitors with blood pressure reducing agents, ACE-inhibitors, angiotensin receptors antagonists, fat level reducing agents, and HMG-CoA reductase inhibitors; CA 2,227,112 discloses the use of NHE-1 inhibitors with sodium-dependent bicarbonate/chloride exchanger (NCBE) inhibitors; CA 2,245,776 discloses the use of NHE-1 inhibitors with, inter alia, β-receptor blockers, calcium antagonists, loop diuretics, thiazide diuretics, potassium-sparing diuretics, aldosterone antagonists, cardiac glycosides, antiarrythmics, $K_{ATP}$ channel openers, $K_{ATP}$ channel blockers, and veratride-activatable sodium channel inhibitors; and commonly assigned PCT International Application Publication No. WO 99/43663 discloses the use of NHE-1 inhibitors with, inter alia, adenosine, adenosine agonists, nitrates, platelet inhibitors, aspirin, dipyridamol, potassium chloride, clonidine, prazosin, and adenosine $A_3$-receptor agonists.

In accordance with the practice of the kits, methods and pharmaceutical compositions of the instant invention, it is believed that the administration of a combination of an NHE-1 inhibitor and a second compound selected from the group consisting of: (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor, will afford greater therapeutic advantages than either of the combination components administered alone.

SUMMARY OF THE INVENTION

The invention provdes methods of reducing tissue damage resulting from ischemia which comprise administering to a mammal in need of such reduction an effective amount of a combination, or a pharmaceutical composition comprising such combination, of an NHE-1 inhibitor and a second compound selected from the group consisting of: (a) a complement modulator, (b) a metabolic modulator, (c) an anti-apoptotic agent, (d) a nitric oxide synthase-related agent, and (e) an enzyme/protein modulator.

The invention further provides pharmaceutical compositions comprising an amount of an NHE-1 inhibitor; an amount of a second compound selected from the group consisting of (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor; and, preferably, a pharmaceutically acceptable pharmaceutically acceptable carrier, vehicle, or diluent.

The invention further provides a kit comprising an amount of a sodium-hydrogen exchanger type-1 inhibitor, and a pharmaceutically acceptable carrier, vehicle, or diluent in a first unit dosage form; an amount of a second compound selected from the group consisting of (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor, and a pharmaceutically acceptable carrier, vehicle, or diluent in a second unit dosage form; and a container.

DETAILED DESCRIPTION OF THE INVENTION

The invention provides methods of reducing tissue damage (e.g., substantially preventing tissue damage and/or inducing tissue protection) resulting from ischemia which methods comprise administering to a mammal (e.g., human male or female) in need of such reduction a therapeutically effective amount of a combination, or a pharmaceutical composition comprising such combination, of a sodium-hydrogen exchanger type 1 (NHE-1 ) inhibitor, and a second compound selected from the group consisting of (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor.

Preferred ischemic tissues that may be treated in accordance with the methods of the present invention comprise those tissues selected from the group consisting of brain, cardiac, liver, kidney, lung, gut, skeletal muscle, spleen, pancreas, nerve, spinal cord, retinal tissue, vasculature, and intestinal tissue. An especially preferred tissue comprises cardiac tissue.

Although any NHE-1 inhibitor may be employed in the methods and pharmaceutical compositions of the present invention, it is generally preferred that such inhibitor be selected from the group consisting of:

(a) a compound of Formula (I)

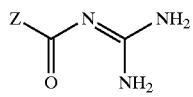

(I)

a prodrug thereof, or a pharmaceutically acceptable salt of the compound or the prodrug thereof; wherein:

Z is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z is carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$) cycloalkyl(C ($C_1$–$C_4$)alkoxy, ($C_1$–$C_4$)alkoxy ($C_1$–$C_4$)alkyl, mono-N- or di-N,N-($C_1$–$C_4$) alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono- or di-substituted independently with hydroxy, ($C_1$–$C_4$) alkoxy, ($C_1$–$C_4$)alklthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N, N-($C_1$–$C_4$)alkylaminosulfonyl; and said ($C_3$–$C_4$) cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$)alkoxy, ($C_1$–$C_4$) alkoxycarbonyl, ($C_1$–$C_4$)alkyl, formyl, ($C_1$–$C_4$) alkanoyl, ($C_1$–$C_4$)alkanoyloxy, ($C_1$–$C_4$) alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$) alkylcarbamoyl, cyano, thiol, ($C_1$–$C_4$)alkylthio, ($C_1$–$C_4$)alkylsulfinyl, ($C_1$–$C_4$)alkylsulfonyl, mono-N- or di-N,N-($C_1$–$C_4$)alkylaminosulfonyl, ($C_2$–$C_4$)alkenyl, ($C_2$–$C_4$)alkynyl or ($C_5$–$C_7$) cycloalkenyl, wherein said ($C_1$–$C_4$)alkoxy, ($C_1$–$C_4$)alkyl, ($C_1$–$C_7$)alkanoyl, ($C_1$–$C_4$)alkylthio, mono-N- or di-N,N-($C_1$–$C_4$)alkylamino or ($C_3$–$C_7$) cycloalkyl $R^6$, $R^7$ and $R^8$ substituents are optionally mono-substituted independently with hydroxy, ($C_1$–$C_4$)alkoxycarbonyl, ($C_3$–$C_7$)cycloalkyl, ($C_1$–$C_4$)alkanoyl, ($C_1$–$C_4$) alkanoylamino, ($C_1$–$C_4$)alkanoyloxy, ($C_1$–$C_4$) alkoxycarbonylamino, sulfonamido, ($C_1$–$C_4$) alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, nitro, ($C_1$–$C_4$)alkylthio, ($C_1$–$C_4$)alkylsulfinyl, ($C_1$–$C_4$)alkylsulfonyl or mono-N- or di-N,N-($C_1$–$C_4$)alkylaminosulfonyl or optionally substituted with one to nine fluorines;

(b) cariporide, or a pharmaceutically acceptable salt thereof;

(c) eniporide, or a pharmaceutically acceptable salt thereof;

(d) BIIB 513, or a pharmaceutically acceptable salt thereof;

(e) TY-12533, or a pharmaceutically acceptable salt thereof; and (f) SM-15681, or a pharmaceutically acceptable salt thereof.

Especially preferred Formula (I) compounds are those compounds selected from the group consisting of:

[1-(2-chlorophenyl)-5-methyl-1H-pyrazole-4-carbonyl] guanidine:

[5-methyl-1-(2-trifluoromethylphenyl)-1H-pyrazole-4-carbonyl]guanidine;

[5-ethyl-1-phenyl-1H-pyrazole-4-carbonyl]guanidine;

[5-cyclopropyl-1-(2-trifluoromethylphenyl)-1H-pyrazole-4-carbonyl]guanidine;

[5-cyclopropyl-1-phenyl-1H-pyrazole-4-carbonyl] guanidine;

[5-cyclopropyl-1-(2,6-dichlorophenyl)-1H-pyrazole-4-carbonyl]guanidine;

[5-methyl-1-(quinolin-6-yl)-1H-pyrazole-4-carbonyl] guanidine;

[5-methyl-1-(naphthalen-1-yl)-1H-pyrazole-4-carbonyl]
  guanidine;
[5-cyclopropyl-1-(quinolin-5-yl)-1H-pyrazole-4-
  carbonyl]guanidine;
[5-cyclopropyl-1-(quinolin-8-yl)-1H-pyrazole-4-
  carbonyl]guanidine;
[3-methyl-1-phenyl-1H-pyrazole-4-carbonyl]guanidine;
[3-methyl-1-(naphthalen-1-yl)-1H-pyrazole-4-carbonyl]
  guanidine;
[3-methyl-1-(isoquinolin-5-yl)-1H-pyrazole-4-carbonyl]
  guanidine;
[2-methyl-5-phenyl-2H-pyrazole-3-carbonyl]guanidine;
[2-methyl-5-(naphthalen-1-yl)-2H-pyrazole-3-carbonyl]
  guanidine;
[5-methyl-2-phenyl-2H-1,2,3-triazole-4-carbonyl]
  guanidine;
[5-methyl-2-(3-methoxyphenyl)-2H-1,2,3-triazole-4-
  carbonyl]guanidine;
[2-(3-bromophenyl)-5-methyl-2H-1,2,3-triazole-4-
  carbonyl]guanidine;
[2-(naphthalen-1-yl)-5-methyl-2H-1,2,3-triazole4-
  carbonyl]guanidine;
[2-(isoquinolin-5-yl)-5-methyl-2H-1,2,3-triazole-4-
  carbonyl]guanidine;
[5-methyl-2-(quinolin-5-yl)-2H-1,2,3-triazole-4-
  carbonyl]guanidine;
[1-(naphthalen-1-yl)-5-cyclopropyl-1H-pyrazole-4-
  carbonyl]guanidine;
[1-(2-chloro-4-methylsulfonylphenyl)-5-cyclopropyl-1H-
  pyrazole-4-carbonyl]guanidine;
[1-(2-chlorophenyl)-5-cyclopropyl-1H-pyrazole-4-
  carbonyl]guanidine;
[1-(2-trifluoromethyl-4-fluorophenyl)-5-cyclopropyl-1H-
  pyrazole-4-carbonyl]guanidine;
[1-(2-bromophenyl)-5-cyclopropyl-1H-pyrazole-4-
  carbonyl]guanidine;
[1-(2-fluorophenyl)-5-cyclopropyl-1H-pyrazole-4-
  carbonyl]guanidine;
[1-(2-chloro-5-methoxyphenyl)-5-cyclopropyl-1H-
  pyrazole-4-carbonyl]guanidine;
[1-(2-chloro4-methylaminosulfonylphenyl)-5-
  cyclopropyl-1H-pyrazole-4-carbonyl]guanidine;
[1-(2,5-dichlorophenyl)-5-cyclopropyl-1H-pyrazole-4-
  carbonyl]guanidine;
[1-(2,3-dichlorophenyl)-5-cyclopropyl-1H-pyrazole-4-
  carbonyl]guanidine;
[1-(2-chloro-5-aminocarbonylphenyl)-5-cyclopropyl-1H-
  pyrazole-4-carbonyl]guanidine;
[1-(2-chloro-5-aminosulfonylphenyl)-5-cyclopropyl-1H-
  pyrazole-4-carbonyl]guanidine;
[1-(2-fluoro-6-trifluoromethylphenyl)-5-cyclopropyl-1H-
  pyrazole-4-carbonyl]guanidine;
[1-(2-chloro-5-methylsulfonylphenyl)-5-cyclopropyl-1H-
  pyrazole-4-carbonyl]guanidine;
[1-(2-chloro-5-dimethylaminosulfonylphenyl)-5-
  cyclopropyl-1H-pyrazole-4-carbonyl]guanidine;
[1-(2-trifluoromethyl-4-chlorophenyl)-5-cyclopropyl-
  1H-pyrazole-4-carbonyl]guanidine;
[1-(8-bromoquinolin-5-yl)-5-cyclopropyl-1H-pyrazole-4-
  carbonyl]guanidine;
[1-(6-chloroquinolin-5-yl)-5-cyclopropyl-1H-pyrazole-4-
  carbonyl]guanidine;
[1-(indazol-7-yl)-5-cyclopropyl-1H-pyrazole-4-carbonyl]
  guanidine;
[1-(benzimidazol-5-yl)-5-cyclopropyl-1H-pyrazole-4-
  carbonyl]guanidine;
[1-(1-isoquinolyl)-5-cyclopropyl-1H-pyrazole-4-
  carbonyl]guanidine;
[5-cyclopropyl-1-(4-quinolinyl)-1H-pyrazole-4-
  carbonyl]guanidine;
[1-(indazol-6-yl)-5-ethyl-1H-pyrazole-4-carbonyl]
  guanidine;
[1-(indazol-5-yl)-5-ethyl-1H-pyrazole-4-carbonyl]
  guanidine;
[1-(benzimidazol-5-yl)-5-ethyl-1H-pyrazole-4-carbonyl]
  guanidine;
[1-(1-methylbenzimidazol-6-yl)-5-ethyl-1H-pyrazole-4-
  carbonyl]guanidine
[1-(5-quinolinyl)-5-n-propyl-1H-pyrazole-4-carbonyl]
  guanidine;
[1-(5-quinolinyl)-5-isopropyl-1H-pyrazole-4-carbonyl]
  guanidine;
[5-ethyl-1-(6-quinolinyl)-1H-pyrazole-4-carbonyl]
  guanidine;
[1-(2-methylbenzimidazol-5-yl)-5-ethyl-1H-pyrazole-4-
  carbonyl]guanidine;
[1-(1,4-benzodioxan-6-yl)-5-ethyl-1H-pyrazole-4-
  carbonyl]guanidine;
[1-(benzotriazol-5-yl)-5-ethyl-1H-pyrazole-4-carbonyl]
  guanidine;
[1-(3-chloroindazol-5-yl)-5-ethyl-1H-pyrazole-4-
  carbonyl]guanidine;
[1-(5-quinolinyl)-5-butyl-1H-pyrazole-4-carbonyl]
  guanidine;
[5-propyl-1-(6-quinolinyl)-1H-pyrazole-4-carbonyl]
  guanidine;
[5-isopropyl-1-(6-quinolinyl)-1H-pyrazole-4-carbonyl]
  guanidine;
[1-(indazol-7-yl)-3-methyl-1H-pyrazole-4-carbonyl]
  guanidine;
[1-(2,1,3-benzothiadiazol-4-yl)-3-methyl-1H-pyrazole-4-
  carbonyl]guanidine; and
[3-methyl-1-(quinolin-5-yl)-1H-pyrazole-4-carbonyl]
  guanidine; the prodrugs thereof, and the pharmaceutically acceptable salts of the compounds, and the prodrugs.

The compounds of Formula (I), the prodrugs thereof, and the pharmaceutically acceptable salts of the compounds and prodrugs, may be prepared as disclosed in the aforementioned, commonly-assigned PCT International Application Publication No. WO 99/43663, the disclosure of which is incorporated herein by reference.

The preferred NHE-1 inhibitor cariporide, i.e. N-(aminoiminomethyl)-4-(1-methylethyl)-3-(methylsulfonyl)-benzamide, may be prepared as disclosed in U.S. Pat. No. 5,591,754, the disclosure of which is incorporated herein by reference. The preferred NHE-1 inhibitor eniporide, i.e. N-(aminoiminomethyl)-2-methyl-5-(methylsulfonyl)-4-(1H-pyrrol-1-yl)-benzamide, may be prepared as disclosed in U.S. Pat. No. 5,753,680, the disclosure of which is incorporated herein by reference. The preferred NHE-1 inhibitor BIIB-513, i.e. N-(aminoiminomethyl)4-(4-(2-furanylcarbonyl)-1-piperazinyl)-3-(methylsulfonyl)-benzamide, may be prepared as disclosed in U.S. Pat. No. 6,114,335, the disclosure of which is incorporated herein by reference. The preferred NHE-1 inhibitor TY-12533, i.e. 6,7,8,9-tetrahydro-2-methyl-5H-cyclohepta[b]pyridine-3-carbonylguanidine, may be prepared as disclosed in PCT International Application Publication No. WO 98/39300, the disclosure of which is incorporated herein by reference. The preferred NHE-1 inhibitor SM-15681, i.e. N-(aminoiminomethyl)-1-methyl-1H-indole-2-carboxamide, may be prepared as disclosed in EPO 0 708 091, the disclosure of which is incorporated herein by reference.

The ability of a compound to function as an NHE-1 inhibitor may be determined according to the protocols described in detail hereinbelow.

A complement modulator refers generally to an agent that modulates, i.e., regulates or inhibits, certain thermolabile substances, normally present in the serum, that are destructive to certain bacteria and other cells sensitized by a specific complement-fixing antibody known as antibody C. Antibody C comprises a group of at least 20 disparate serum proteins, the activity of which is affected by a series of interactions resulting in enzymatic cleavages which can follow at least two distinct pathways. The complement pathways contribute to myocardial ischemia-reperfusion injury in vivo, ostensibly via a combination of mechanisms including, but not limited to, stimulation of cytokine release from various cell types, expression of adhesion molecules, and neutrophil infiltration, of which all mechanisms directly elicit cell death. Accordingly, it is believed that the administration of a combination of an NHE-1 inhibitor and a complement modulator will afford greater protection from tissue damage resulting from ischemia than either agent administered alone.

Although any complement modulator may be employed in the methods and pharmaceutical compositions of the instant invention, it is generally preferred that such complement modulator be selected from the group consisting of a C5a inhibitor, preferably L-747981, or a pharmaceutically acceptable salt thereof, a soluble complement receptor type 1 (sCR1) inhibitor, or an analog thereof, preferably amidinophenylpyruvic acid (APPA), and a C1 esterase inhibitor.

The preferred C5a inhibitor L-747981, the chemical structure of which is shown hereinbelow, and the pharmaceutically acceptable salts thereof, may be prepared according to known synthetic methods.

L-747891

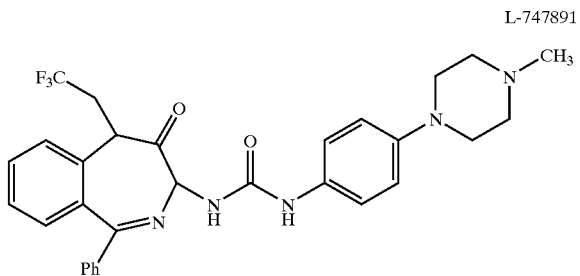

The ability of L-747981 to selectively bind to the C5a receptor is disclosed in Flanagan, K. L., et al., ACS, 210th Chicago: MEDI 085 (1995). The preferred soluble complement receptor type I (sCRI) inhibitor amidinophenylpyruvic acid (APPA), may be obtained commercially.

The ability of a compound to inhibit C5a may be determined according to the methodology set forth in Vakeva, A. P., et al., Circulation, 97 (22), 2259–67 (1998). The ability of a compound to inhibit complement activation at the sCR1 receptor may be determined according to the protocols described by Rittershaus, C. W., J. Biol. Chem., 274 (16), 11237–44 (1999). The ability of a compound to inhibit C1 esterase may be determined according to the methodology disclosed in Benny, A. G., et al., Haematologia, 22(3), 189–93 (1989).

Generally, the term metabolic modulator refers generally to any agent that serves to modulate, i.e., regulate, stimulate, or inhibit, one or more metabolic pathways. With respect to the methods and pharmaceutical compositions of the present invention, metabolic modulators such as pyruvate dehydrogenase kinase inhibitors, for example, dichloroacetate (DCA), activate the myocardial dehydrogenase (PDC) complex, thus increasing glucose oxidation and decreasing fatty acid oxidation in the ischemic myocardium. Accordingly, reduction of ischemic tissue damage by treatment with a combination of an NHE-1 inhibitor and a metabolic modulator should elicit additional cardioprotective benefit.

Although any metabolic modulator may be employed in the methods and pharmaceutical compositions of the instant invention, it is generally preferred that such modulator be selected from the group consisting of a pyruvate dehydrogenase complex up-regulator/activator, preferably dichloroacetate (DCA), a pyruvate dehydrogenase kinase inhibitor, preferably DCA, a malonyl CoA decarboxylase inhibitor, an acetyl CoA carboxylase activator, a partial fatty acid oxidation (pFOX) inhibitor, preferably ranolazine or trimetazidine, a 5' AMP-activated protein kinase (AMPK) inhibitor, a carnitine palmitoyl transferase inhibitor, preferably etomoxir, and a fatty acid CoA synthase inhibitor, preferably triascin C. The preferred pFOX inhibitors ranolazine and trimetazidine may be prepared as disclosed in U.S. Pat. Nos. 4,567,264, and 4,663,325 respectively, which patents are incorporated herein in their entirety by reference. The preferred carnitine palmitoyl transferase inhibitor etomoxir may be prepared as disclosed in U.S. Pat. No. 4,337,267, the disclosure of which is incorporated herein by reference. The preferred fatty acid CoA synthase inhibitor triascin C, i.e. (2E,4E,7E)-undecatrienal-nitrosohydrazone, may be prepared as disclosed in U.S. Pat. No. 4,297,096, the disclosure of which is incorporated herein by reference.

The ability of a compound to function as a pyruvate dehydrogenase complex up-regulator/activator, a pyruvate dehydrogenase kinase inhibitor, or a malonyl CoA decarboxylase inhibitor, may be determined according to the methodologies disclosed in Stanley, W. C., et al., J. Mol. Cell. Cardiol., 28, 905–914 (1996). The ability of a compound to function as an acetyl CoA carboxylase activator may be determined according to the protocols described in Belke, D. D., et al., Biochem. Biophys. Acta, 1391 (1), 25–36 (1998). The ability of a compound to function as a partial fatty acid oxidation (pFOX) inhibitor may be determined according to the procedures of McCormack J. G., et al., J. Appl. Physiol., 81/2, 905–910 (1996), or Merrill G. F., et al., Am. J. Physiol., 273, E1107–1112 (1997). The ability of a compound to function as a carnitine palmitoyl transferase inhibitor may be determined according to the methodology disclosed in Kudo, et al., J. Biol. Chem., 270, 17513–17520 (1995). The ability of a compound to function as a 5' AMP-activated protein kinase (AMPK) inhibitor may be determined according to Haystead T. A., et al., Eur. J. Biochem., 187, 199–205 (1990). The ability of a compound to function as a fatty acid CoA synthase inhibitor may be determined according to the following systems.

Oxidase/Catalase Coupling System:

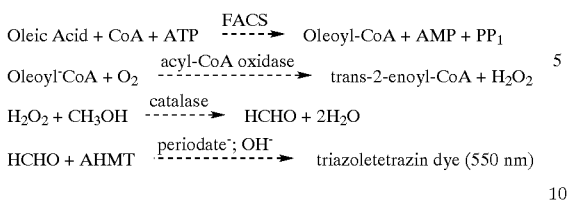

A reduction in absorbance at 550 nm indicates fatty acid CoA synthase inhibition.

Pyrophosphatase Coupling System:

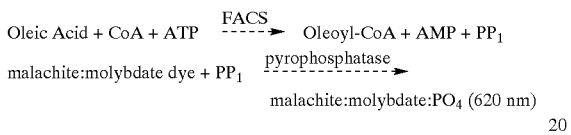

A reduction in absorbance at 620 nm indicates fatty acid CoA synthase inhibition.

Generally, an anti-apoptotic agent inhibits apoptosis, i.e., programmed cell death, the process by which certain cells self-destruct by fragmentation into membrane-bound particles which are subsequently phagocytized by other cells, for example, macrophages. Because apoptosis is known to occur during myocardial ischemia-reperfusion injury, it is believed that enzymatic inhibition of the apoptotic cascade with an anti-apoptic agent, in combination with treatment with an NHE-1 inhibitor, will confer greater protection from tissue damage resulting from ischemia than either agent administered alone.

Although any anti-apoptotic agent may be employed in the methods and pharmaceutical compositions of the present invention, it is generally preferred that such anti-apoptotic agent comprise a caspase inhibitor. The term caspase inhibitor refers to any agent that inhibits the activity of caspases, a salient family of enzymes involved in the induction of apoptosis in mammalian cells, for example, excessive apoptosis of cardiac myocytes during reperfusion, and neuronal cells during ischemia. Generally preferred caspase inhibitors, useful in the methods and pharmaceutical compositions of the instant invention, comprise those compounds selected from the group consisting of a compound of structural Formula (II)

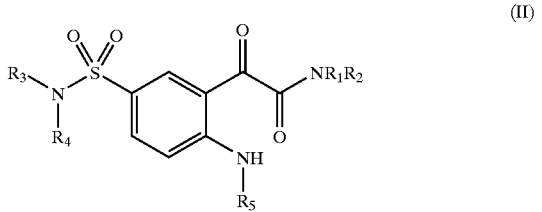

(II)

wherein $R_1$ and $R_2$, together with the nitrogen to which they are attached, form a 4- to 7-membered ring; $R_3$ and $R_4$, together with the nitrogen atom to which they are attached, form a 4- to 7-membered ring; and R is benzoyl, or ($C_{1-6}$)alkyl; and a compound of structural Formula (III)

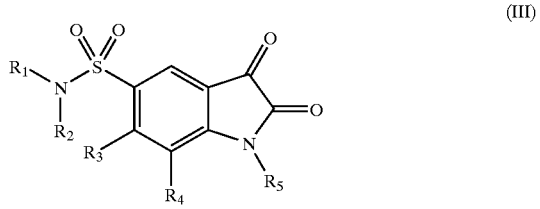

(III)

wherein $R_1$ is hydrogen, or ($C_{1-4}$)alkyl; $R_2$ is ($C_{1-10}$)alkyl, optionally substituted with aryl($C_{1-4}$)alkyl, optionally substituted heteroaryl($C_{1-4}$)alkyl, optionally substituted ($C_{3-7}$)cycloalkyl, or $R_1$ and $R_2$, together with the nitrogen to which they are attached, form a 3- to 10-membered ring which optionally contains an additional heteroatom selected from oxygen, nitrogen, or sulfur; $R_3$ and $R_4$ are ($C_{1-6}$)alkyl, hydrogen, nitro, or halogen; and $R_5$ is ($C_{1-6}$)alkyl, hydrogen, arylalkyl, or heteroarylalkyl.

The preferred caspase inhibitors of structural Formula (II) may be prepared as described in PCT International Application Publication No. WO 99/65451. The preferred caspase inhibitors of structural Formula (III) may be prepared as described in PCT International Application Publication No. WO 99/06367.

The ability of a compound to inhibit apoptosis may be determined according to the methodology of Wu, J. C., et al., Methods, 17 (4), 320–8 (1999). The ability of an agent to function as a caspase inhibitor may be determined according to the methodologies disclosed in the aforementioned PCT International Application Publication Nos. WO 99/06367 and WO 99/65451.

The term nitric oxide synthase-related agent, as employed within the context of the instant invention, refers generally to any agent that regulates, i.e., inhibits, promotes, or enhances, the enzymatic formation of nitric oxide (NO) free-radical, a known mediator of cell-to-cell communication and potent vasodilator, which free-radical is produced by the nitric oxide synthase-catalyzed reaction of L-arginine with 2 $O_2$ and 1.5 NADPH. Because certain agents increase the expression of inducible nitric oxide synthase (iNOS, i.e., Type 3), the nitric oxide produced by this enzyme, or that generated by nitric oxide donors, is currently believed to be cardioprotective. Furthermore, NO produced acutely by endothelial NOS (Type 2), or neuronal NOS (Type 1) during ischemia-reperfusion injury is also believed to be cardioprotective. For detailed discussions of the cardioprotective effects of NO produced by nitric oxide donors, see, for example, Takano, H., et al., Circ. Res., 83, 73–84 (1998) and Pabla, R., et al., Heart Circ. Physiol. 38, H1113–1121 (1995). In direct contrast, it has been further disclosed that the inhibition of NO, through the activity of NOS inhibitors, also affords protection against ischemic injury. See, for example, Depre, C., et al., Circulation, 92, 1911–1918 (1995) and Woolfson, R. G., et al., Circulation, 91, 1545–1551 (1995). Accordingly, it is believed that treatment with a nitric oxide synthase-related agent, in combination with an NHE-1 inhibitor, will confer greater protection from tissue damage resulting from ischemia than either agent administered alone.

Although any nitric oxide synthase-related agent may be employed in the methods and pharmaceutical compositions of the present invention, it is generally preferred that such agent be selected from the group consisting of monophosphoryl lipid A, or an analog thereof, preferably RC-552 (MPL-C) or ONO4007, a nitric oxide donor, preferably nipride, and a nitric oxide synthase inhibitor, preferably aminoguanidine or N(G)-monomethyl-L-arginine (L-NMMA).

The preferred monophosphoryl lipid A analog ONO-4077, i.e. (S)-2-deoxy-2-((1-oxo-3-((1-oxo-9-phenylnonyl) oxy)-tetradecyl)amino)-, 3-benzenenonanoate 4-(hydrogen sulfate)-D-glucose, may be prepared as disclosed in U.S. Pat. Nos. 5,294,723 and 5,733,927, the disclosures of which are incorporated herein by reference. The preferred nitric oxide donor nipride, i.e., sodium nitrosylpentacyanoferrate (II), may be prepared as described in Playfair, L., Proc. Roy. Soc. London 5, 846 (1849). The preferred nitric oxide synthase inhibitor aminoguanidine may be prepared as described in Smith, G. B. L., et al., J. Am. Chem. Soc., 57, 2730 (1935). The preferred nitric oxide inhibitor N(C)-monomethyl-L-arginine (L-NMMA) may be obtained from commercial sources.

The ability of an agent to function as a nitric oxide donor, nitric oxide synthase activator, or nitric oxide synthase inhibitor may be determined according to the methods disclosed in Rees, D. D., et al., British Journal of Pharmacology, 101, 746–52 (1990), and Archer, S., FASEB Journal, 7, 349–60 (1999).

In the practice of the methods and pharmaceutical compositions of the invention, the NHE-1 inhibitor may further be employed in combination with an enzyme/protein modulator selected from the group consisting of a protein kinase C ε activator, an endothelin converting enzyme inhibitor, preferably S-17162, a tissue-activated fibrinolytic (TAFI), a $Na^+/Ca^{+2}$ exchanger isoform-1 (NCX-1) inhibitor, preferably KB-R7943, and a poly (ADP ribose) synthetase (PARS/PARP) inhibitor, preferably 3-aminobenzamide, or a compound, or a pharmaceutically acceptable salt, prodrug, active metabolite, or solvate thereof, of Formula (IV)

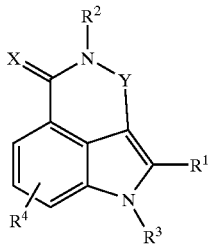

(IV)

wherein
$R^1$ is H, halogen, cyano, an optionally substituted alkyl, alkenyl, alkynyl, cycloalkyl, heterocycloalkyl, aryl, or heteroaryl group;
or —C(O)—$R^{10}$, where $R^{10}$ is hydrogen, an optionally substituted alkyl, alkenyl, alkynyl, cycloalkyl, heterocycloalkyl, aryl, or heteroaryl group;
or —$OR^{100}$ or $NR^{100}R^{110}$, where $R^{100}$ and $R^{110}$ are each independently H or an optionally substituted alkyl, alkenyl, alkynyl, cycloalkyl, heterocycloalkyl, aryl, or heteroaryl group;
$R^2$ is H or alkyl;
$R^3$ is H or alkyl;
$R^4$ is H, halogen or alkyl;
X is O or S; and
Y is $(CR^5R^6)(CR^7R^8)_n$ or N=C($R^5$), where n is 0 or 1; $R^5$ and $R^6$ are each independently H or an optionally substituted alkyl, alkenyl, alkynyl, cycloalkyl, heterocycloalkyl, aryl, or heteroaryl group; and $R^7$ and $R^8$ are each independently H or an optionally substituted alky, alkenyl, alkynyl, cycloalkyl, heterocycloalkyl, aryl, or heteroaryl group.

The term protein kinase C ε refers to the cytoplasmic, calcium-activated family of kinases that are believed to be downstream mediators of, inter alia, the ischemic preconditioning pathway. Accordingly, because activators of this enzyme are cardioprotective, reduction of ischemic tissue damage by treatment with a combination of an NHE-1 inhibitor and a protein kinase C ε activator should provide additional cardioprotective benefit. Endothelin is known to contribute to myocardial ischemia-reperfusion injury and, therefore, by preventing endothelin production with an endothelin converting enzyme inhibitor, reduction of ischemic tissue damage by treatment with a combination of an NHE-1 inhibitor and an endothelin converting enzyme inhibitor should provide additional cardioprotective advantages. Tissue-activated fibrinolytic inhibitors are known to be useful in the treatment of both deep venous thrombosis (DVT) and acute coronary syndrome (ACS), a syndrome that embraces, inter alia, ischemic attack. Accordingly, reduction of ischemic tissue damage by treatment with a combination of an NHE-1 inhibitor and a TAFI inhibitor should elicit additional cardioprotective benefit. During cardiac reperfusion, $Na^+/Ca^{+2}$ exchanger isoform-1 (NCX-1) increases intracellular calcium levels, due to the increased intracellular sodium levels resulting from NHE-1 activity, which leads to contracture, arrhythmias, and cellular death. Thus, inhibition of NCX-1 is cardioprotective and, therefore, reduction of ischemic tissue damage by treatment with a combination of an NHE-1 inhibitor and an NCX-1 inhibitor should elicit additional cardioprotective benefit. PARS/PARP is a DNA repair enzyme that is activated during myocardial ischemia/reperfusion injury in response to DNA single strand breaks. The enzyme consumes intracellular $NAD^+$ and ATP pools, and slows the rate of glycolysis and mitochondrial respiration which can contribute to, or directly cause, cardiomyocyte dysfunction and/or death. Accordingly, PARS/PARP inhibitors are believed to be cardioprotective and, therefore, reduction of ischemic tissue damage by treatment with a combination of an NHE-1 inhibitor and a PARS/PARP inhibitor should elicit additional cardioprotective benefit.

The preferred endothelin converting enzyme inhibitor S-17162, i.e. N-(2,3-dihydroxypropylphosphonyl-(S)-Leu-(S)-Trp-OH, disodium salt, may be prepared as disclosed in U.S. Pat. Nos. 5,481,030, 5,591,728, and 5,608,045, the disclosures of which are hereby incorporated by reference in their entirety. The preferred $Na^+/Ca^{+2}$ exchanger isoform-1 (NCX-1) inhibitor KB-R7943, i.e., (2-(2-(4-(4-nitrobenzyloxy)-phenyl)-ethyl)-isothiourea methanesulfonate), may be prepared as described in PCT International Application Publication No. WO 97/09306. The preferred poly (ADP ribose) synthetase (PARS/PARP) inhibitor 3-aminobenzamide is available commercially. The preferred poly (ADP ribose) synthetase (PARS/PARP) inhibitors of Formula (IV) may be prepared as disclosed in PCT International Application Publication No. WO 2000/42040.

The ability of an agent to function as a protein kinase C ε activator may be determined according to the protocol disclosed in Bowling, N., et al., Circulation, 99, 384–91 (1999). The ability of an agent to function as an endothelin converting enzyme inhibitor may be determined according to Fassina, G., et al., Peptide Res., 6, 73–78 (1993). The ability of an agent to function as a tissue-activated fibrinolytic inhibitor (TAFI) inhibitor may be determined according to Bajzar, L., et al., J. Biol, Chem., 270, 14477–14484 (1995). The ability of an agent to function as a Na$^+$/Ca$^{+2}$ exchanger isoform-1 (NCX-1) inhibitor may be determined according to the methodology described by Iwamoto, T., et al., Am. J. Physiol., 275, C423–430 (1998). The ability of an agent to function as a poly (ADP ribose) synthetase (PARS/PARP) inhibitor may be determined according to the methodologies of Decker, P., et al., Clinical Cancer Research, 5, 1169–1172 (1999).

Generally, the NHE-1 inhibitor can be administered to a mammal at dosage levels in the range of from about 0.001 to about 100 mg/kg body weight per day. For a normal adult human having a body weight of about 70 kg, a dosage in the range of from about 0.01 to about 50 mg/kg body weight is typically preferred. However, some variability in these general dosage ranges may be required depending upon the age and weight of the mammal being treated, the intended route of administration, the particular agent being administered, and the like. The determination of dosage ranges and optimal dosages for a particular mammal is within the ability of one of ordinary skill in the art having the benefit of the instant disclosure.

The dosage of the complement modulator, metabolic modulator, anti-apoptotic agent, nitric oxide synthase-related agent, or enzyme/protein modulator will also be generally dependent upon a number of factors including the health of the mammal being treated, the extent of treatment desired, the nature and kind of concurrent therapy, if any, and the frequency of treatment and the nature of the effect desired. In general, dosage ranges of complement modulators, metabolic modulators, anti-apoptotic agents, nitric oxide synthase-related agents, and enzyme/protein modulators range from about 0.001 to about 250 mg/kg body weight per day. For a normal adult human having a body weight of about 70 kg, a dosage in the range of from about 0.1 to about 25 mg/kg body weight is typically preferred. However, some variability in this general dosage range may be required depending upon the age and weight of the subject being treated, the intended route of administration, the particular agent being administered and the like. The determination of dosage ranges and optimal dosages for a particular mammal is also well within the ability of one of ordinary skill in the art having the benefit of the instant disclosure.

According to the methods of the invention, the combination of the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na /Ca+2 exchanger isoform-1 (NCX-1) inhibitor, and a poly (ADP ribose) synthetase (PARS/PARP) inhibitor is administered to a mammal in need of treatment therewith, preferably in the form of a pharmaceutical composition. In the combination aspect of the invention, the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na$^+$/Ca$^{+2}$ exchanger isoform-1 (NCX-1) inhibitor, and a poly (ADP ribose) synthetase (PARS/PARP) inhibitor may be administered either separately or in the pharmaceutical composition comprising both. It is generally preferred that such administration be oral. However, if the subject being treated is unable to swallow, or oral administration is otherwise impaired or undesirable, parenteral or transdermal administration will be appropriate.

According to the methods of the invention, when the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na$^+$/Ca$^{+2}$ exchanger isoform-1 (NCX-1) inhibitor, and a poly (ADP ribose) synthetase (PARS/PARP) inhibitor are administered together, such administration can be sequential in time or simultaneous with the simultaneous method being generally preferred. For sequential administration, the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na$^+$/Ca$^{+2}$ exchanger isoform-1 (NCX-1) inhibitor, and a poly (ADP ribose) synthetase (PARS/PARP) inhibitor can be administered in any order. It is generally preferred that such administration be oral. It is especially preferred that such administration be oral and simultaneous. When the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na$^+$/Ca$^{+2}$ exchanger isoform-1 (NCX-1) inhibitor, and a poly (ADP ribose) synthetase (PARS/PARP) inhibitor are administered sequentially, the administration of each can be by the same or by different methods.

According to the methods of the invention, the combination of the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na$^+$/Ca$^{+2}$ exchanger isoform-1 (NCX-1) inhibitor, and a poly (ADP ribose) synthetase (PARS/PARP) inhibitor is preferably administered in the form of a pharmaceutical composition comprising a pharmaceutically acceptable carrier, vehicle, or diluent. Accordingly, the combination of the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a Na$^+$/Ca$^{+2}$ exchanger isoform-1 (NCX-1) inhibitor, and a poly (ADP ribose) synthetase (PARS/PARP) inhibitor can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection may comprise pharmaceutically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, the active compound is admixed with at least one inert customary pharmaceutical excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents.

Suspensions, in addition to the active compound, may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration preferably comprise suppositories, which can be prepared by mixing a compound of the present invention with suitable non-irritating excipients or carriers such as cocoa butter, polyethylene glycol or a suppository wax, which are solid at ordinary room temperature, but liquid at body temperature, and therefore, melt in the rectal cavity thereby releasing the active component.

Dosage forms for topical administration of the NHE-1 inhibitor, and the second compound selected from the group consisting of a complement modulator, a metabolic modulator, an anti-apoptotic agent, a nitric oxide synthase-related agent, and an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor may comprise ointments, powders, sprays and inhalants. The active agent or agents are admixed under sterile condition with a pharmaceutically acceptable carrier, and any preservatives, buffers, or propellants that may be required.

The combinations and pharmaceutical compositions comprising the combinations of the present invention are useful as therapeutants or prophylactic agents for diseases caused or aggravated by the acceleration of the sodium/hydrogen (Na+/H+) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g., congestive heart failure, acute heart failure, cardiac hypertrophy, etc.), restenosis after PTCA, PTCI, shock (e.g., hemorrhagic shock, endotoxin shock, etc.)], renal diseases (e.g., diabetes mellitus, diabetic nephropathy, ischemic acute renal failure, etc.) organ disorders associated with ischemia or ischemic reperfusion [(e.g., heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g., ischemic stroke, hemorrhagic stroke, etc.), cerebro ischemic disorders (e.g., disorders associated with cerebral infarction, disorders caused after cerebral apoplexy as sequelae, or cerebral edema. The combinations and pharmaceutical compositions of this invention can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries.

Preferably, the combinations and pharmaceutical compositions of this invention can be used to for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the combinations and pharmaceutical compositions of this invention can be used for myocardial protection in patients presenting with ongoing cardiac (acute coronary syndromes, e.g., myocardial infarction or unstable angina) or cerebral ischemic events (e.g., stroke).

Preferably, the combinations and pharmaceutical compositions of this invention can be used for chronic myocardial protection in patients with diagnosed coronary heart disease (e.g., previous myocardial infarction or unstable angina) or patients who are at high risk for myocardial infarction (age greater than 65 and two or more risk factors for coronary heart disease).

The utility of the combinations and pharmaceutical compositions of the present invention as medical agents in the treatment of diseases, such as are detailed herein in mammals (e.g., humans) for example, in patients presenting with ongoing cardiac or cerebral ischemic events, or chronic cardioprotection in patients with diagnosed coronary heart disease, or at risk for coronary heart disease, cardiac dysfunction or myocardial stunning is demonstrated by the activity of the combinations and pharmaceutical compositions of this invention in conventional preclinical cardioprotection assays [see, for example, the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays may also provide a means whereby the activities of the combinations and pharmaceutical compositions of this invention can be compared with the activities of other known compounds. The results of these comparisons are useful for determining dosage levels in mammals, including humans, for the treatment of such diseases.

Since the present invention relates to methods of reducing tissue damage resulting from ischemia with a combination of active ingredients that may be administered separately, the invention further relates to combining separate pharmaceutical compositions in kit form. The kit, according to the instant invention, comprises an amount of a sodium-hydrogen exchanger type-1 (NHE-1) inhibitor, and a pharmaceutically acceptable carrier, vehicle, or diluent in a first unit dosage form; an amount of a second compound selected from the group consisting of (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor, and a pharmaceutically acceptable carrier, vehicle, or diluent in a second unit dosage form; and a container. The container is employed to contain the separate components and may comprise, for example, a divided bottle or a divided foil packet, however, the separate compositions may also be contained within a single, undivided container. Normally, the kit will also include directions for the administration of the separate components. The kit form is particularly advantageous when the separate components are administered in different dosage forms (e.g., oral and parenteral), are administered at different dosage levels, or when titration of the individual components of the combination is desired by the prescribing physician.

One example of such a kit is a so-called blister pack. Blister packs are well known in the packaging industry and are used widely for the packaging of pharmaceutical unit dosage forms (tablets, capsules, and the like). Blister packs generally comprise a sheet of relatively rigid material covered with a foil of a preferably transparent plastic material. During the packaging process, recesses (e.g., blisters) are formed in the plastic foil. The recesses generally conform to the size and shape of the tablets or capsules to be contained therein. Next, the tablets or capsules are placed in the recesses and the sheet of relatively rigid material is sealed against the plastic foil at the face of the foil which is opposite from the direction in which the recesses were formed. As a result, the tablets or capsules are captively retained and sealed inside the recesses between the plastic foil and the sheet. Preferably, the strength of the sheet is such that the tablets or capsules may be removed from the blister pack by the application of manual pressure on the outer surface of the recesses whereby an opening is formed in the sheet at the place of the recess. The tablet or capsule can then be removed through the formed opening.

It is further desirable to provide a memory aid on the pack, for example, in the form of numbers or similar indicia proximate to the tablets or capsules whereby the indicia correspond to the days of the regimen which the dosage form so specified is to be ingested. An additional example of such a memory aid is a calendar printed on the pack, for example, as follows: "First Week, Monday, Tuesday, . . . etc. . . . Second Week, Monday, Tuesday, . . . " etc. In light of the instant disclosure, other variations will be readily apparent to one of ordinary skill in the art. A "daily dose" can be a single tablet or capsule, or multiple tablets or capsules, or tablets or capsules to be ingested on a given day. Also, a daily dose of the sodium-hydrogen exchanger type 1 (NHE-1) inhibitor can consist of a single tablet or capsule, while a daily dose of the second compound, selected from the group consisting of (a) a compliment modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor, can consist of multiple tablets or capsules, and vice-versa. The memory aid should reflect this.

In another specific embodiment of the invention, a pack designed to dispense the daily doses one at a time in the order of their intended use is provided. Preferably, the pack is equipped with a memory aid, so as to further facilitate compliance with the dosage regimen. An example of such a memory aid comprises a mechanical counter that indicates the number of daily doses to be dispensed, Another example of such a memory aid comprises a battery-powered microchip memory coupled with a liquid crystal readout, or audible reminder signal which, for example, reads out the date and time that the last daily dose has been taken and/or reminds the patient when the next dose is to be taken.

Measurement of Human NHE-1 Inhibitory Activity

Methodologies for measurement of human NHE-1 activity and inhibitor potency are predicated on those published by Watson et al., Am. J. Physiol., 24;G222g–G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 min at 37° C. with the pH sensitive fluorescent probe BCECF (5 $\mu$M; Molecular Probes, Eugene, Oreg.). BCECF loaded cells are incubated for 30 min at 37° C. in acid loading media (70 mM choline chloride, 50 mM $NHCl_4$, 5 mM KCl, 1 mM $MgCl_2$, 1.8 mM $CaCl_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM $MgCl_2$, 1.8 mM $CaCl_2$, 5 mM glucose, 10 mM HEPES, pH 7.5)±test compound, and NHE-mediated recovery of intracellular pH is monitored as the subsequent time-dependent increase BCECF fluorescence. The potency of human NHE-1 inhibitors is calculated as the concentration that reduces recovery of intracellular pH by 50% ($IC_{50}$).

As background information, it is noted that brief periods of myocardial ischemia followed by coronary artery reperfusion protects the heart from subsequent severe myocardial ischemia (Murry et al., Circulation 74:1124–1136,1986).

The therapeutic effects of the combinations and pharmaceutical compositions of this invention in preventing heart tissue damage resulting from an ischemic insult can be demonstrated in vitro along lines presented in Tracey, et al. (Cardiovasc. Res., 33: 410–415, 1997), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Tracey, et al., Cardiovasc. Res., 33: 410–415, 1997). The in vitro test described below demonstrates that the combinations and pharmaceutical compositions of the invention can also pharmacologically induce cardioprotection, i.e., reduced myocardial infarct size, when administered to a rabbit isolated heart. The effects of the combinations and pharmaceutical compositions are compared to ischemic preconditioning and the A1 adenosine agonist, PIA ($N^6$-1-(phenyl-2R-isopropyl) adenosine), that has been shown to pharmacologically induce cardioprotection in the rabbit isolated heart (Tracey, et al., Cardiovasc. Res., 33: 410–415, 1997). The exact methodology is described below.

The protocol used for these experiments closely follows that described by Tracey, et al., Cardiovasc. Res., 33: 410–415, 1997. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a prominent branch of the left coronary artery, approximately ⅔ of the distance towards the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure $\leq$10 mm Hg. Total coronary flow is also continuously monitored using an in-line flow probe and normalized for heart weight.

The heart is allowed to equilibrate for 30 min, over which time the heart must show stable left ventricular pressures within the parameters outlined above. If the heart rate falls below 180 bpm at any time prior to the 30 min. period of regional ischemia, the heart is paced at about 200 bpm for the remainder of the experiment. Ischemic preconditioning is induced by total cessation of cardiac perfusion (global ischemia) for 5 min, followed by reperfusion for 10 min. The regional ischemia is provided by tightening the snare around the coronary artery branch. Following the 30 min regional ischemia, the snare is released and the heart reperfused for an additional 120 min.

Pharmacological cardioprotection is induced by infusing the combination or pharmaceutical composition at predetermined concentrations, starting 30 min prior to the 30 min regional ischemia, and continuing until the end of the 120 min reperfusion period. Hearts which receive test combinations or pharmaceutical compositions do not undergo the period of ischemic preconditioning. A reference compound, PIA (25 nM) is perfused through hearts (which do not receive the test combination or pharmaceutical composition) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 $\mu$m) Duke Scientific Corp.(Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at −20° C. The next day, the heart is sliced into 2 mm transverse sections from the apex to the top of the ventricles. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (% IA/AAR). All data are expressed as mean±SE and compared statistically using a Mann-Whitney non-parametric test with a Bonferroni correction for multiple comparisons. Significance is considered as $p<0.05$.

The therapeutic effects of the combinations and pharmaceutical compositions of this invention in preventing heart tissue damage otherwise resulting from an ischemic insult can also be demonstrated in vivo along lines presented in Liu et al. (Circulation, 84: 350–356, 1991) as described specifically herein. This in vivo assay tests the cardioprotection of the combinations and pharmaceutical compositions relative to the control group which receives saline vehicle. Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether combinations and pharmaceutical compositions can pharmacologically induce cardioprotection, i.e., reduced myocardial infarct size, when parenterally administered to intact, anesthetized rabbits. The effects of the combinations and pharmaceutical compositions of this invention can be compared to ischemic preconditioning using the Al adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991). The methodology is described below.

Surgery: New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allows the affected area to reperfuse. Myocardial ischemia is evidenced by regional cyanosis; reperfusion is evidenced by reactive hyperemia.

Protocol: Once arterial pressure and heart rate have been stable for at least 30 min. the test is started. Ischemic preconditioning is induced by occluding the coronary artery for 5 min followed by a 10 min. reperfusion. Pharmacological preconditioning is induced by infusing test combination or pharmaceutical composition over, for example 5 min. and allowing 10 min. before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The combination or pharmaceutical composition and PIA are dissolved in saline or other suitable vehicle and delivered at 1 to 5 mg/kg, respectively.

Staining (Liu et al., Circulation 84:350–356, 1991): At the end of the 2 hour reperfusion period, the hearts are quickly removed, hung on a Langendorff apparatus, and flushed for 1 minute with normal saline heated to body temperature (38° C.). The silk suture used as the snare is then tied tightly to reocclude the artery and a 0.5% suspension of fluorescent zinc cadmium sulphate particles (1–10 µm) Duke Scientific Corp. (Palo Alto, Calif.) is infused with the perfusate to stain all of the myocardium except the area at risk (nonfluorescent ventricle). The hearts are then quickly frozen and stored overnight at –20° C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (% IA/MR). All data are expressed as Mean±SEM and compared statistically using single factor ANOVA or Mann Whitney non-parametric test. Significance is considered as $p<0.05$.

The combinations and pharmaceutical compositions of this invention can be tested for their utility in reducing or preventing ischemic injury in non-cardiac tissues, for example, the brain, or the liver, utilizing procedures reported in the scientific literature. The combinations and pharmaceutical compositions of this invention in such tests can be administered by the preferred route and vehicle of administration and at the preferred time of administration either prior to the ischemic episode, during the ischemic episode, following the ischemic episode (reperfusion period) or during any of the below-mentioned experimental stages.

The benefit of the combinations and pharmaceutical compositions of the invention in reducing ischemic brain damage can be demonstrated, for example, in mammals using the method of Park, et al (Ann. Neurol. 1988;24:543–551). According to the procedure of Park, et al., adult male Sprague Dawley rats are anesthetized initially with 2% halothane, and thereafter by mechanical ventilation with a nitrous oxide-oxygen mixture (70%:30%) containing 0.5–1% halothane. A tracheostomy is then performed. The stroke volume of the ventilator is adjusted to maintain arterial carbon dioxide tension at approximately 35 mm Hg and adequate arterial oxygenation ($PaO_2$>90 mm Hg). Body temperature can be monitored by a rectal thermometer, and the animals can be maintained normothermic, if necessary, by external heating. The animals next undergo subtemporal craniectomy to expose the main trunk of the left middle cerebral artery (MCA) under an operating microscope, and the exposed artery is occluded with microbipolar coagulation to generate large ischemic lesions in the cerebral cortex and basal ganglia. After three hours of MCA occlusion, the rats are deeply anesthetized with 2% halothane and a thoracotomy is performed to infuse heparinized saline into the left ventricle. The effluent is collected via an incision of the right atrium. The saline washout is followed by approximately 200 ml of a 40% formaldehyde, glacial acetic acid and absolute methanol solution (FAM; 1:1:8, v/v/v), then the animals are decapitated and the head is stored in fixative for 24 hours. The brain is then removed, dissected, embedded in paraffin wax, and sectioned (approximately 100 sections 0.2 mm per brain). The sections are then stained with hematoxylin-eosin or with a combination of cresyl violet and Luxol fast blue, and examined by light microscopy to identify and quantitate the ischemic damage using a precalibrated image analyzer. The ischemic volumes and areas are expressed in absolute units ($mm^3$ and $mm^2$) and as a percentage of the total region examined. The effect of the combinations and pharmaceutical compositions of this invention to reduce ischemic brain damage induced by MCA occlusion is noted based on a reduction in the area or volume of relative or absolute ischemic damage in the brain sections from the rats in the treatment group compared to brain sections from rats in a placebo-treated control group.

Other methods which could alternatively be utilized to demonstrate the benefit of the combinations and pharmaceutical compositions of the invention in reducing ischemic brain damage include those described by Nakayama, et al. in Neurology 1988,38:1667–1673; Memezawa, et al. in Stroke 1992,23:552–559; Folbergrova, et al. in Proc. Natl. Acad. Sci 1995,92:5057–5059; and Gotti, et al. in Brain Res. 1990,522:290–307.

The benefit of the combinations and pharmaceutical compositions of this invention to reduce ischemic liver damage can be demonstrated, for example, in mammals using the method of Yokoyama, et al. (Am. J. Physiol. 1990;258:G564–G570). According to the procedure of Yokoyama, et al., fasted adult male Sprague Dawley rats are anesthetized with sodium pentobarbital (40 mg/kg i.p.), then the animals are tracheotomized and mechanically ventilated with room air. The liver is extirpated and placed in an environmental chamber maintained at constant temperature (37° C.), then perfused through the portal vein at a constant pressure of 15 cm $H_2O$ with a modified, hemoglobin-free Krebs-Henseleit buffer (in mM: 118 NaCl, 4.7 KCl, 27 $NaHCO_3$, 2.5 $CaCl_2$, 1.2 $MSO_4$, 1.2 $KH_2PO_4$, 0.05 EDTA, and 11 mM glucose, plus 300 U heparin). The pH of the perfusate is maintained at 7.4 by gassing the buffer with 95% $O_2$–5% $CO_2$. Each liver is perfused at a flow rate of 20 ml/min in a single-pass manner for a 30 min washout and equilibration period (preischemic period), followed by a 2 hour period of global ischemia, and then a 2 hour period of reperfusion under conditions identical to the preischemic period. Aliquots (20 ml) of the perfusate are collected during the preischemic period, immediately after the occlusive ischemic period, and every 30 min of the 2 hour reperfusion period. The perfusate samples are assayed for the appearance of hepatocellular enzymes, for example, aspartate amino-transferase (AST), alanine amino-transferase (ALT), and lactate dehydrogenase (LDH), which are taken to quantitatively reflect the degree of ischemic liver tissue damage during the procedure. AST, ALT, and LDH activities in the perfusate can be determined by several methods, for example, by the reflectometry method using an automatic Kodak Ektachem 500 analyzer reported by Nakano, et al. (Hepatology 1995;22:539–545). The effect of the combinations and pharmaceutical compositions of this invention in reducing ischemic liver damage induced by occlusion is noted based on a reduction in the release of hepatocellular enzymes immediately following the occlusive period and/or during the postischemic-reperfusion period in the perfused livers from the rats in the treatment group compared to perfused livers from rats in a placebo-treated control group.

Other methods which may be utilized to demonstrate the benefits of the compositions and methods of this invention in reducing ischemic liver damage include those described by Nakano, et al. (Hepatology 1995;22;539–545).

What is claimed is:

1. A pharmaceutical composition comprising an amount of a sodium-hydrogen exchanger type-1 inhibitor, and an amount of a second compound selected from the group consisting of (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a $Na^+/Ca^{+2}$ exchanger isoform-1 (NCX-1) inhibitor, and a poly (ADP ribose) synthetase (PARS/PARP) inhibitor.

2. A pharmaceutical composition according to claim 1 further comprising a pharmaceutically acceptable carrier, vehicle, or diluent.

3. A pharmaceutical composition according to claim 1 wherein said sodium-hydrogen exchanger type 1 (NHE-1) inhibitor is selected from the group consisting of:

(a) a compound of Formula (I)

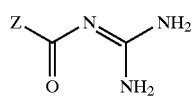

a prodrug thereof, or a pharmaceutically acceptable salt of the compound or the prodrug thereof; wherein:

Z is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z is carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono- or di-substituted independently with hydroxy, ($C_1$–$C_4$)alkoxy, ($C_1$–$C_4$)alklthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$)alkoxy, ($C_1$–$C_4$)alkoxycarbonyl, ($C_1$–$C_4$)alkyl, formyl, ($C_1$–$C_4$)alkanoyl, ($C_1$–$C_4$)alkanoyloxy, ($C_1$–$C_4$)alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, ($C_1$–$C_4$)alkylthio, ($C_1$–$C_4$)alkylsulfinyl, ($C_1$–$C_4$)alkylsulfonyl, mono-N- or di-N,N-($C_1$–$C_4$)alkylaminosulfonyl, ($C_2$–$C_4$)alkenyl, ($C_2$–$C_4$)alkynyl or ($C_5$–$C_7$)cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$ cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N- $(C_1-C_4)$alkylamino, carbamoyl, mono-N- or di-N,N-$(C_1-C_4)$alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N- $(C_1-C_4)$alkylaminosulfonyl or optionally substituted with one to nine fluorines;

(b) cariporide, or a pharmaceutically acceptable salt thereof;
(c) eniporide, or a pharmaceutically acceptable salt thereof:
(d) BIIB 513, or a pharmaceutically acceptable salt thereof;
(e) TY-12533, or a pharmaceutically acceptable salt thereof; and
(f) SM-15681, or a pharmaceutically acceptable salt thereof.

4. A pharmaceutical composition according to claim 3 wherein said compound of Formula (I) is a compound selected from the group consisting of:

[1-(2-chlorophenyl)-5-methyl-1H-pyrazole-4-carbonyl] guanidine;
[5-methyl-1-(2-trifluoromethylphenyl)-1H-pyrazole-4-carbonyl]guanidine;
[5-ethyl-1-phenyl-1H-pyrazole-4-carbonyl]guanidine;
[5-cyclopropyl-1-(2-trifluoromethylphenyl)-1H-pyrazole-4-carbonyl]guanidine;
[5-cyclopropyl-1-phenyl-1H-pyrazole-4-carbonyl] guanidine;
[5-cyclopropyl-1-(2,6-dichlorophenyl)-1H-pyrazole-4-carbonyl]guanidine;
[5-methyl-1-(quinolin-6-yl)-1H-pyrazole-4-carbonyl] guanidine;
[5-methyl-1-(naphthalen-1-yl)-1H-pyrazole-4-carbonyl] guanidine;
[5-cyclopropyl-1-(quinolin-5-yl)-1H-pyrazole-4-carbonyl]guanidine;
[5-cyclopropyl-1-(quinolin-8-yl)-1H-pyrazole-4-carbonyl]guanidine;
[3-methyl-1-phenyl-1H-pyrazole-4-carbonyl]guanidine;
[3-methyl-1-(naphthalen-1-yl)-1H-pyrazole-4-carbonyl] guanidine;
[3-methyl-1-(isoquinolin-5-yl)-1H-pyrazole-4-carbonyl] guanidine;
[2-methyl-5-phenyl-2H-pyrazole-3-carbonyl]guanidine;
[2-methyl-5-(naphthalen-1-yl)-2H-pyrazole-3-carbonyl] guanidine;
[5-methyl-2-phenyl-2H-1,2,3-triazole-4-carbonyl] guanidine;
[5-methyl-2-(3-methoxyphenyl)-2H-1,2,3-triazole-4-carbonyl]guanidine;
[2-(3-bromophenyl)-5-methyl-2H-1,2,3-triazole-4-carbonyl]guanidine;
[2-(naphthalen-1-yl)-5-methyl-2H-1,2,3-triazole-4-carbonyl]guanidine;
[2-(isoquinolin-5-yl)-5-methyl-2H-1,2,3-triazole4-carbonyl]guanidine;
[5-methyl-2-(quinolin-5-yl)-2H-1,2,3-triazole4-carbonyl] guanidine;
[1-(naphthalen-1-yl)-5-cyclopropyl-1H-pyrazole-4-carbonyl]guanidine;
[1-(2-chloro-4-methylsulfonylphenyl)-5-cyclopropyl-1H-pyrazole-4-carbonyl]guanidine;
[1-(2-chlorophenyl)-5-cyclopropyl-1H-pyrazole-4-carbonyl]guanidine;
[1-(2-trifluoromethyl-4-fluorophenyl)-5-cyclopropyl-1H-pyrazole-4-carbonyl]guanidine;
[1-(2-bromophenyl)-5-cyclopropyl-1H-pyrazole-4-carbonyl]guanidine;
[1-(2-fluorophenyl)-5-cyclopropyl-1H-pyrazole-4-carbonyl]guanidine;
[1-(2-chloro-5-methoxyphenyl)-5-cyclopropyl-1H-pyrazole-4-carbonyl]guanidine;
[1-(2-chloro-4-methylaminosulfonylphenyl)-5-cyclopropyl-1H-pyrazole-4-carbonyl]guanidine;
[1-(2,5-dichlorophenyl)-5-cyclopropyl-1H-pyrazole-4-carbonyl]guanidine;
[1-(2,3-dichlorophenyl)-5-cyclopropyl-1H-pyrazole-4-carbonyl]guanidine;
[1-(2-chloro-5-aminocarbonylphenyl)-5-cyclopropyl-1H-pyrazole-4-carbonyl]guanidine;
[1-(2-chloro-5-aminosulfonylphenyl)-5-cyclopropyl-1H-pyrazole-4-carbonyl]guanidine;
[1-(2-fluoro-6-trifluoromethylphenyl)-5-cyclopropyl-1H-pyrazole-4-carbonyl]guanidine;
[1-(2-chloro-5-methylsulfonylphenyl)-5-cyclopropyl-1H-pyrazole-4-carbonyl]guanidine;
[1-(2-chloro-5-dimethylaminosulfonylphenyl)-5-cyclopropyl-1H-pyrazole-4-carbonyl]guanidine;
[1-(2-trifluoromethyl-4-chlorophenyl)-5-cyclopropyl-1H-pyrazole-4-carbonyl]guanidine;
[1-(8-bromoquinolin-5-yl)-5-cyclopropyl-1H-pyrazole-4-carbonyl]guanidine;
[1-(6-chloroquinolin-5-yl)-5-cyclopropyl-1H-pyrazole-4-carbonyl]guanidine;
[1-(indazol-7-yl)-5-cyclopropyl-1H-pyrazole-4-carbonyl] guanidine;
[1-(benzimidazol-5-yl)-5-cyclopropyl-1H-pyrazole-4-carbonyl]guanidine;
[1-(1-isoquinolyl)-5-cyclopropyl-1H-pyrazole-4-carbonyl]guanidine;
[5-cyclopropyl-1-(4-quinolinyl)-1H-pyrazole-4-carbonyl]guanidine;
[1-(indazol-6-yl)-5-ethyl-1H-pyrazole-4-carbonyl] guanidine;
[1-(indazol-5-yl)-5-ethyl-1H-pyrazole-4-carbonyl] guanidine;
[1-(benzimidazol-5-yl)-5-ethyl-1H-pyrazole-4-carbonyl] guanidine;
[1-(1-methylbenzimidazol-6-yl)-5-ethyl-1H-pyrazole-4-carbonyl]guanidine
[1-(5-quinolinyl)-5-n-propyl-1H-pyrazole-4-carbonyl] guanidine;
[1-(5-quinolinyl)-5-isopropyl-1H-pyrazole-4-carbonyl] guanidine;
[5-ethyl-1-(6-quinolinyl)-1 H-pyrazole-4-carbonyl] guanidine;

[1-(2-methylbenzimidazol-5-yl)-5-ethyl-1H-pyrazole-4-carbonyl]guanidine;
[1-(1,4-benzodioxan-6-yl)-5-ethyl-1H-pyrazole-4-carbonyl]guanidine;
[1-(benzotriazol-5-yl)-5-ethyl-1H-pyrazole-4-carbonyl] guanidine;
[1-(3-chloroindazol-5-yl)-5-ethyl-1H-pyrazole-4-carbonyl]guanidine;
[1-(5-quinolinyl)-5-butyl-1H-pyrazole-4-carbonyl] guanidine;
[5-propyl-1-(6-quinolinyl)-1H-pyrazole-4-carbonyl] guanidine;
[5-isopropyl-1-(6-quinolinyl)-1H-pyrazole-4-carbonyl] guanidine;
[1-(indazol-7-yl)-3-methyl-1H-pyrazole-4-carbonyl] guanidine;
[1-(2,1,3-benzothiadiazol-4-yl)-3-methyl-1H-pyrazole-4-carbonyl]guanidine; and
[3-methyl-1-(quinolin-5-yl)-1H-pyrazole-4-carbonyl] guanidine; the prodrugs thereof, and the pharmaceutically acceptable salts of the compounds, and the prodrugs.

5. A pharmaceutical composition according to claim 1 wherein said complement modulator is selected from the group consisting of a C5a inhibitor, a soluble complement receptor type-1 (sCR1) inhibitor, or an analog thereof, and a C1 esterase inhibitor.

6. A pharmaceutical composition according to claim 5 wherein said C5a inhibitor is L-747981, or a pharmaceutically acceptable salt thereof, and said soluble complement receptor type 1 (sCR1) inhibitor is amidinophenylpyruvic acid (APPA).

7. A pharmaceutical composition according to claim 1 wherein said metabolic modulator is selected from the group consisting of a pyruvate dehydrogenase complex up-regulator/activator, a pyruvate dehydrogenase kinase inhibitor, a malonyl CoA decarboxylase inhibitor, an acetyl CoA carboxylase activator, a partial fatty acid oxidation (pFOX) inhibitor, a 5' AMP-activated protein kinase (AMPK) inhibitor, a carnitine palmitoyl transferase inhibitor, and a fatty acid CoA synthase inhibitor.

8. A method according to claim 7 wherein said pyruvate dehydrogenase complex up-regulator/activator and said pyruvate dehydrogenase kinase inhibitor are dichloroacetate (DCA), said partial fatty acid oxidation (pFOX) inhibitor is ranolazine or trimetazidine, said carnitine palmitoyl transferase inhibitor is etomoxir, and said fatty acid CoA synthase inhibitor is triascin C.

9. A pharmaceutical composition according to claim 1 wherein said anti-apoptotic agent is a caspase inhibitor.

10. A pharmaceutical composition according to claim 9 wherein said caspase inhibitor is a compound selected from the group consisting of a compound of Formula (II)

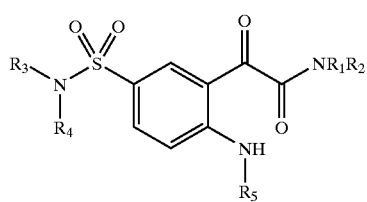

(II)

wherein
$R_1$ and $R_2$, together with the nitrogen to which they are attached, form a 4- to 7-membered ring; $R_3$ and $R_4$, together with the nitrogen atom to which they are attached, form a 4- to 7-membered ring; and R is benzoyl, or $(C_{1-6})$alkyl; and
a compound of Formula (III)

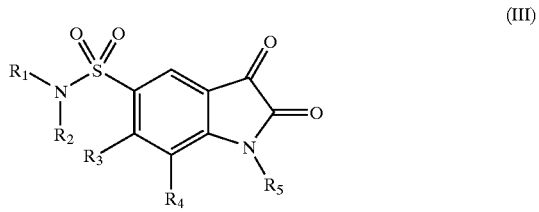

(III)

wherein
$R_1$ is hydrogen, or $(C_{1-4})$alkyl; $R_2$ is $(C_{1-10})$alkyl, optionally substituted with aryl$(C_{1-4})$alkyl, optionally substituted heteroaryl$(C_{1-4})$alkyl, optionally substituted $(C_{1-7})$cycloalkyl, or $R_1$ and $R_2$, together with the nitrogen to which they are attached, form a 3- to 10-membered ring which optionally contains an additional heteroatom selected from oxygen, nitrogen, or sulfur; $R_3$ and $R_4$ are $(C_{1-6})$alkyl, hydrogen, nitro, or halogen; and $R_5$ is $(C_{1-6})$alkyl, hydrogen, arylalkyl, or heteroarylalkyl.

11. A pharmaceutical composition according to claim 1 wherein said nitric oxide synthase-related agent is selected from the group consisting of monophosporyl lipid A, or an analog thereof, a nitric oxide donor, and a nitric oxide synthase activator.

12. A pharmaceutical composition according to claim 11 wherein said monophosporyl lipid A, or said analog thereof is RC-552 (MPL-C) or ONO-4007, said nitric oxide donor is nipride, and said nitric oxide synthase inhibitor is aminoguanidine or N(G)-monomethyl-L-arginine (L-NMMA).

13. A pharmaceutical composition according to claim 1 wherein said endothelin converting enzyme inhibitor is S-17162, said $Na^+/Ca^{+2}$ exchanger isoform-1 (NCX-1) inhibitor is KB-R7943, and said poly (ADP ribose) synthetase (PARS/PARP) inhibitor is 3-aminobenzamide, or a compound, or a pharmaceutically acceptable salt, prodrug, active metabolite, or solvate thereof, of Formula (IV)

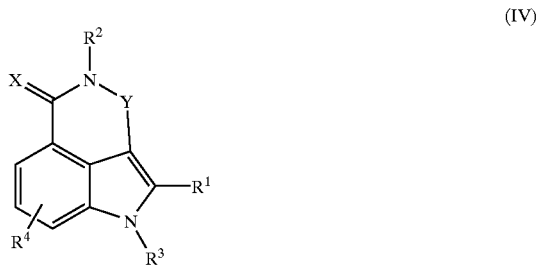

(IV)

wherein
$R^1$ is H, halogen, cyano, an optionally substituted alkyl, alkenyl, alkynyl, cycloalkyl, heterocycloalkyl, aryl, or heteroaryl group;
or —C(O)—$R^{10}$ where $R^{10}$ is hydrogen, an optionally substituted alkyl, alkenyl, alkynyl, cycloalkyl, heterocycloalkyl, aryl, or heteroaryl group;
or —$OR^{100}$ or $NR^{100}R^{110}$, where $R^{100}$ and $R^{110}$ are each independently H or an optionally substituted alkyl, alkenyl, alkynyl, cycloalkyl, heterocycloalkyl, aryl, or heteroaryl group;

R² is H or alkyl;

R³ is H or alkyl;

R⁴ is H, halogen or alkyl;

X is O or S; and

Y is $(CR^5R^6)(CR^7R^8)_n$ or $N=C(R^5)$, where n is 0 or 1; R⁵ and R⁶ are each independently H or an optionally substituted alkyl, alkenyl, alkynyl, cycloalkyl, heterocycloalkyl, aryl, or heteroaryl group; and R⁷ and R⁸ are each independently H or an optionally substituted alky, alkenyl, alkynyl, cycloalkyl, heterocycloalkyl, aryl, or heteroaryl group.

14. A kit comprising an amount of a sodium-hydrogen exchanger type-1 inhibitor, and a pharmaceutically acceptable carrier, vehicle, or diluent in a first unit dosage form; an amount of a second compound selected from the group consisting of (a) a complement modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a Na⁺/Ca⁺² exchanger isoform-1 (NCX-1) inhibitor, and a poly (ADP ribose) synthetase (PARS/PARP) inhibitor, and a pharmaceutically acceptable carrier, vehicle, or diluent in a second unit dosage form; and a container.

15. A method of reducing tissue damage resulting from ischemia which method comprises administering to a mammal in need of such treatment an effective amount of a pharmaceutical composition of claim 1.

16. A method according to claim 15 wherein said tissue is selected from the group consisting of brain, cardiac, liver, kidney, lung, gut, skeletal muscle, spleen, pancreas, nerve, spinal cord, retinal tissue, vasculature, and intestinal tissue.

17. A method according to claim 16 wherein said tissue is cardiac tissue.

18. A method of reducing tissue damage resulting from ischemia which method comprises administering to a mammal in need of such reduction a therapeutically effective amount of a combination comprising a sodium-hydrogen exchanger type 1 (NHE-1) inhibitor, and an effective amount of a second compound selected from the group consisting of (a) a compliment modulator, (b) a metabolic modulator, (c) an anti-apoptotic agent, (d) a nitric oxide synthase-related agent, and (e) an enzyme/protein modulator selected from the group consisting of a protein kinase C activator, an endothelin converting enzyme inhibitor, a tissue-activated fibrinolytic inhibitor (TAFI), a Na⁺/Ca⁺² exchanger isoform-1 (NCX-1) inhibitor, and a poly (ADP ribose) synthetase (PARS/PARP) inhibitor.

19. A method according to claim 18 wherein said tissue is selected from the group consisting of brain, cardiac, liver, kidney, lung, gut, skeletal muscle, spleen, pancreas, nerve, spinal cord, retinal tissue, vasculature, and intestinal tissue.

20. A method according to claim 19 wherein said tissue is cardiac tissue.

21. A method according to claim 18 wherein said sodium-hydrogen exchanger type 1 (NHE-1) inhibitor is selected from the group consisting of:

(a) a compound of Formula (I)

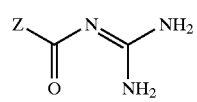

(I)

a prodrug thereof, or a pharmaceutically acceptable salt of the compound or the prodrug thereof; wherein:

Z is carbon connected and is a five-membered, diaza, diunsaturated ring having two contiguous nitrogens, said ring optionally mono-, di-, or tri-substituted with up to three substituents independently selected from R¹, R² and R³; or Z is carbon connected and is a five-membered, triaza, diunsaturated ring, said ring optionally mono- or di-substituted with up to two substituents independently selected from R⁴ and R⁵;

wherein R¹, R², R³, R⁴ and R⁵ are each independently hydrogen, hydroxy($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono- or di-substituted independently with hydroxy, ($C_1$–$C_4$)alkoxy, ($C_1$–$C_4$)alklthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M is optionally substituted, on one ring if the moiety is monocyclic, or one or both rings if the moiety is bicyclic, on carbon or nitrogen with up to three substituents independently selected from R⁶, R⁷ and R⁸, wherein one of R⁶, R⁷ and R⁸ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally R⁶, R⁷ and R⁸ are optionally hydroxy, nitro, halo, ($C_1$–$C_4$)alkoxy, ($C_1$–$C_4$)alkoxycarbonyl, ($C_1$–$C_4$)alkyl, formyl, ($C_1$–$C_4$)alkanoyl, ($C_1$–$C_4$)alkanoyloxy, ($C_1$–$C_4$)alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, ($C_1$–$C_4$)alkylthio, ($C_1$–$C_4$)alkylsulfinyl, ($C_1$–$C_4$)alkylsulfonyl, mono-N- or di-N,N-($C_1$–$C_4$)alkylaminosulfonyl, ($C_2$–$C_4$)alkenyl, ($C_2$–$C_4$)alkynyl or ($C_5$–$C_7$)

cycloalkenyl, wherein said $(C_1-C_4)$alkoxy, $(C_1-C_4)$alkyl, $(C_1-C_7)$alkanoyl, $(C_1-C_4)$alkylthio, mono-N- or di-N,N-$(C_1-C_4)$alkylamino or $(C_3-C_7)$cycloalkyl $R^6$, $R^7$ and $R^8$ substituents are optionally mono- substituted independently with hydroxy, $(C_1-C_4)$alkoxycarbonyl, $(C_3-C_7)$ cycloalkyl, $(C_1-C_4)$alkanoyl, $(C_1-C_4)$ alkanoylamino, $(C_1-C_4)$alkanoyloxy, $(C_1-C_4)$ alkoxycarbonylamino, sulfonamido, $(C_1-C_4)$ alkylsulfonamido, amino, mono-N- or di-N,N-$(C_1-C_4)$alkylamino, carbamoyl, mono-N- or di-N, N-$(C_1-C_4)$alkylcarbamoyl, cyano, thiol, nitro, $(C_1-C_4)$alkylthio, $(C_1-C_4)$alkylsulfinyl, $(C_1-C_4)$ alkylsulfonyl or mono-N- or di-N,N-$(C_1-C_4)$ alkylaminosulfonyl or optionally substituted with one to nine fluorines;
- (b) cariporide, or a pharmaceutically acceptable salt thereof;
- (c) eniporide, or a pharmaceutically acceptable salt thereof;
- (d) BIIB 513, or a pharmaceutically acceptable salt thereof;
- (e) TY-12533, or a pharmaceutically acceptable salt thereof; and
- (f) SM-15681, or a pharmaceutically acceptable salt thereof.

22. A method according to claim 21 wherein said compound of Formula (I) is a compound selected from the group consisting of:

[1-(2-chlorophenyl)-5-methyl-1H-pyrazole-4-carbonyl] guanidine;

[5-methyl-1-(2-trifluoromethylphenyl)-1H-pyrazole-4-carbonyl]guanidine;

[5-ethyl-1-phenyl-1H-pyrazole-4-carbonyl]guanidine;

[5-cyclopropyl-1-(2-trifluoromethylphenyl)-1H-pyrazole-4-carbonyl]guanidine:

[5-cyclopropyl-1-phenyl-1H-pyrazole-4-carbonyl] guanidine;

[5-cyclopropyl-1-(2,6-dichlorophenyl)-1H-pyrazole-4-carbonyl]guanidine;

[5-methyl-1-(quinolin-6-yl)-1H-pyrazole-4-carbonyl] guanidine;

[5-methyl-1-(naphthalen-1-yl)-1H-pyrazole-4-carbonyl] guanidine;

[5-cyclopropyl-1-(quinolin-5-yl)-1H-pyrazole-4-carbonyl]guanidine;

[5-cyclopropyl-1-(quinolin-8-yl)-1H-pyrazole-4-carbonyl]guanidine;

[3-methyl-1-phenyl-1H-pyrazole-4-carbonyl]guanidine;

[3-methyl-1-(naphthalen-1-yl)-1H-pyrazole-4-carbonyl] guanidine;

[3-methyl-1-(isoquinolin-5-yl)-1H-pyrazole-4-carbonyl] guanidine;

[2-methyl-5-phenyl-2H-pyrazole-3-carbonyl]guanidine;

[2-methyl-5-(naphthalen-1-yl)-2H-pyrazole-3-carbonyl] guanidine;

[5-methyl-2-phenyl-2H-1,2,3-triazole4-carbonyl] guanidine;

[5-methyl-2-(3-methoxyphenyl)-2H-1,2,3-triazole-4-carbonyl]guanidine;

[2-(3-bromophenyl)-5-methyl-2H-1,2,3-triazole-4-carbonyl]guanidine;

[2-(naphthalen-1-yl)-5-methyl-2H-1,2,3-triazole-4-carbonyl]guanidine;

[2-(isoquinolin-5-yl)-5-methyl-2H-1,2,3-triazole-4-carbonyl]guanidine;

[5-methyl-2-(quinolin-5-yl)-2H-1,2,3-triazole-4-carbonyl]guanidine;

[1-(naphthalen-1-yl)-5-cyclopropyl-1H-pyrazole-4-carbonyl]guanidine;

[1-(2-chloro-4-methylsulfonylphenyl)-5-cyclopropyl-1H-pyrazole-4-carbonyl]guanidine;

[1-(2-chlorophenyl)-5-cyclopropyl-1H-pyrazole-4-carbonyl]guanidine;

[1-(2-trifluoromethyl-4-fluorophenyl)-5-cyclopropyl-1H-pyrazole-4-carbonyl]guanidine;

[1-(2-bromophenyl)-5-cyclopropyl-1H-pyrazole-4-carbonyl]guanidine;

[1-(2-fluorophenyl)-5-cyclopropyl-1H-pyrazole-4-carbonyl]guanidine;

[1-(2-chloro-5-methoxyphenyl)-5-cyclopropyl-1H-pyrazole-4-carbonyl]guanidine;

[1-(2-chloro-4-methylaminosulfonylphenyl)-5-cyclopropyl-1H-pyrazole-4-carbonyl]guanidine;

[1-(2,5-dichlorophenyl)-5-cyclopropyl-1H-pyrazole-4-carbonyl]guanidine;

[1-(2,3-dichlorophenyl)-5-cyclopropyl-1H-pyrazole-4-carbonyl]guanidine;

[1-(2-chloro-5-aminocarbonylphenyl)-5-cyclopropyl-1H-pyrazole-4-carbonyl]guanidine;

[1-(2-chloro-5-aminosulfonylphenyl)-5-cyclopropyl-1H-pyrazole-4-carbonyl]guanidine;

[1-(2-fluoro-6-trifluoromethylphenyl)-5-cyclopropyl-1H-pyrazole-4-carbonyl]guanidine;

[1-(2-chloro-5-methylsulfonylphenyl)-5-cyclopropyl-1H-pyrazole-4-carbonyl]guanidine;

[1-(2-chloro-5-dimethylaminosulfonylphenyl)-5-cyclopropyl-1H-pyrazole-4-carbonyl]guanidine;

[1-(2-trifluoromethyl-4-chlorophenyl)-5-cyclopropyl-1H-pyrazole-4-carbonyl]guanidine:

[1-(8-bromoquinolin-5-yl)-5-cyclopropyl-1H-pyrazole-4-carbonyl]guanidine;

[1-(6-chloroquinolin-5-yl)-5-cyclopropyl-1H-pyrazole-4-carbonyl]guanidine;

[1-(indazol-7-yl)-5-cyclopropyl-1H-pyrazole-4-carbonyl] guanidine;

[1-(benzimidazol-5-yl)-5-cyclopropyl-1H-pyrazole-4-carbonyl]guanidine;

[1-(1-isoquinolyl)-5-cyclopropyl-1H-pyrazole-4-carbonyl]guanidine;

[5-cyclopropyl-1-(4-quinolinyl)-1H-pyrazole-4-carbonyl]guanidine;

[1-(indazol-6-yl)-5-ethyl-1H-pyrazole-4-carbonyl] guanidine;

[1-(indazol-5-yl)-5-ethyl-1H-pyrazole-4-carbonyl] guanidine;

[1-(benzimidazol-5-yl)-5-ethyl-1H-pyrazole-4-carbonyl] guanidine;

[1-(1-methylbenzimidazol-6-yl)-5-ethyl-1H-pyrazole-4-carbonyl]guanidine

[1-(5-quinolinyl)-5-n-propyl-1H-pyrazole-4-carbonyl] guanidine;

[1-(5-quinolinyl)-5-isopropyl-1H-pyrazole-4-carbonyl] guanidine;

[5-ethyl-1-(6-quinolinyl)-1H-pyrazole-4-carbonyl] guanidine;

[1-(2-methylbenzimidazol-5-yl)-5-ethyl-1H-pyrazole-4-carbonyl]guanidine:

[1-(1,4-benzodioxan-6-yl)-5-ethyl-1H-pyrazole-4-carbonyl]guanidine;

[1-(benzotriazol-5-yl)-5-ethyl-1H-pyrazole-4-carbonyl]guanidine;

[1-(3-chloroindazol-5-yl)-5-ethyl-1H-pyrazole-4-carbonyl]guanidine;

[1-(5-quinolinyl)-5-butyl-1H-pyrazole-4-carbonyl]guanidine:

[5-propyl-1-(6-quinolinyl)-1H-pyrazole-4-carbonyl]guanidine;

[5-isopropyl-1-(6-quinolinyl)-1H-pyrazole-4-carbonyl]guanidine;

[1-(indazol-7-yl)-3-methyl-1H-pyrazole-4-carbonyl]guanidine;

[1-(2,1,3-benzothiadiazol-4-yl)-3-methyl-1H-pyrazole-4-carbonyl]guanidine; and

[3-methyl-1-(quinolin-5-yl)-1H-pyrazole-4-carbonyl]guanidine; the prodrugs thereof, and the pharmaceutically acceptable salts of the compounds, and the prodrugs.

23. A method according to claim 18 wherein said complement modulator is selected from the group consisting of a C5a inhibitor, a soluble complement receptor type 1 (sCR1) inhibitor, or an analog thereof, and a C1 esterase inhibitor.

24. A method according to claim 23 wherein said C5a inhibitor is L-747981, or a pharmaceutically acceptable salt thereof, and said soluble complement receptor type 1 (sCR1) inhibitor is amidinophenylpyruvic acid (APPA).

25. A method according to claim 18 wherein said metabolic modulator is selected from the group consisting of a pyruvate dehydrogenase complex up-regulator/activator, a pyruvate dehydrogenase kinase inhibitor, a malonyl CoA decarboxylase inhibitor, an acetyl CoA carboxylase activator, a partial fatty acid oxidation (pFOX) inhibitor, a 5' AMP-activated protein kinase (AMPK) inhibitor, a carnitine palmitoyl transferase inhibitor, and a fatty acid CoA synthase inhibitor.

26. A method according to claim 8 wherein said pyruvate dehydrogenase complex up-regulator/activator and said pyruvate dehydrogenase kinase inhibitor are dichloroacetate (DCA), said partial fatty acid oxidation (pFOX) inhibitor is ranolazine or trimetazidine, said carnitine palmitoyl transferase inhibitor is etomoxir, and said fatty acid CoA synthase inhibitor is triascin C.

27. A method according to claim 18 wherein said anti-apoptotic agent is a caspase inhibitor.

28. A method according to claim 10 wherein said caspase inhibitor is a compound selected from the group consisting of a compound of Formula (11)

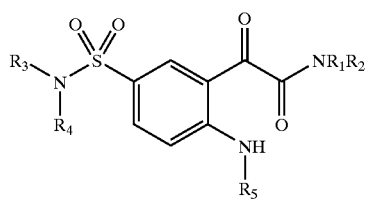

(II)

wherein
R$_1$ and R$_2$, together with the nitrogen to which they are attached, form a 4- to 7-membered ring; R$_3$ and R$_4$, together with the nitrogen atom to which they are attached, form a 4- to 7-membered ring; and R is benzoyl, or (C$_{1-6}$)alkyl; and a compound of Formula (III)

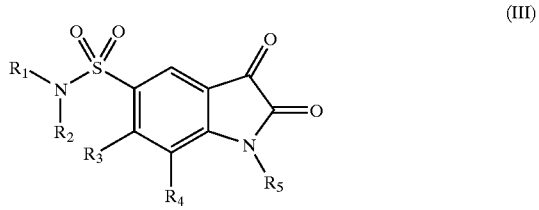

(III)

wherein
R$_1$ is hydrogen, or (C$_{1-4}$)alkyl; R$_2$ is (C$_{1-10}$)alkyl, optionally substituted with aryl(C$_{1-4}$)alkyl, optionally substituted heteroaryl(C$_{1-4}$)alkyl, optionally substituted (C$_{3-7}$)cycloalkyl, or R$_1$ and R$_2$, together with the nitrogen to which they are attached, form a 3- to 10-membered ring which optionally contains an additional heteroatom selected from oxygen, nitrogen, or sulfur; R$_3$ and R$_4$ are (C$_{1-6}$)alkyl, hydrogen, nitro, or halogen; and R5 is (C$_{1-6}$)alkyl, hydrogen, arylalkyl, or heteroarylalkyl.

29. A method according to claim 18 wherein said nitric oxide synthase-related agent is selected from the group consisting of monophosporyl lipid A, or an analog thereof, a nitric oxide donor, and a nitric oxide synthase activator.

30. A method according to claim 29 wherein said monophosporyl lipid A, or said analog thereof is RC-552 (MPL-C) or ONO4007, said nitric oxide donor is nipride, and said nitric oxide synthase inhibitor is aminoguanidine or N(G)-monomethyl-L-arginine (L-NMMA).

31. A method according to claim 18 wherein said endothelin converting enzyme inhibitor is S-17162, said Na$^+$/Ca$^{+2}$ exchanger isoform-1 (NCX-1) inhibitor is KB-R7943, and said poly (ADP ribose) synthetase (PARS/PARP) inhibitor is 3-aminobenzamide, or a compound, or a pharmaceutically acceptable salt, prodrug, active metabolite, or solvate thereof, of Formula (IV)

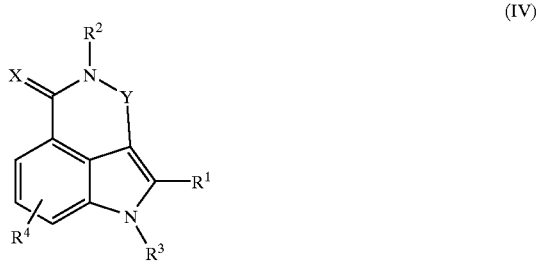

(IV)

wherein
R$^1$ is H, halogen, cyano, an optionally substituted alkyl, alkenyl, alkynyl, cycloalkyl, heterocycloalkyl, aryl, or heteroaryl group;
or —C(O)—R$^{10}$, where R$^{10}$ is hydrogen, an optionally substituted alkyl, alkenyl, alkynyl, cycloalkyl, heterocycloalkyl, aryl, or heteroaryl group;
or —OR$^{100}$ or NR$^{100}$R$^{110}$, where R$^{100}$ and R$^{110}$ are each independently H or an optionally substituted alkyl, alkenyl, alkynyl, cycloalkyl, heterocycloalkyl, aryl, or heteroaryl group;

$R^2$ is H or alkyl;

$R^3$ is H or alkyl;

$R^4$ is H, halogen or alkyl;

X is O or S; and

Y is $(CR^5R^6)(CR^7R^8)_n$ or $N=C(R^5)$, where n is 0 or 1; $R^5$ and $R^6$ are each independently H or an optionally substituted alkyl, alkenyl, alkynyl, cycloalkyl, heterocycloalkyl, aryl, or heteroaryl group; and $R^7$ and $R^8$ are each independently H or an optionally substituted alky, alkenyl, alkynyl, cycloalkyl, heterocycloalkyl, aryl, or heteroaryl group.

* * * * *